United States Patent [19]

Torii et al.

[11] 4,163,111
[45] Jul. 31, 1979

[54] 2-CYCLOPENTENONE DERIVATIVES

[75] Inventors: Sigeru Torii; Hideo Tanaka; Yuichi Kobayashi, all of Okayama, Japan

[73] Assignee: Otsuka Kagaku Yakuhim Kabushiki Kaisha, Osaka, Japan

[21] Appl. No.: 913,745

[22] Filed: Jun. 8, 1978

[30] Foreign Application Priority Data

Aug. 12, 1977 [JP] Japan ................................ 52/97171
Aug. 12, 1977 [JP] Japan ................................ 52/97172

[51] Int. Cl.² ........................ C07C 69/74; C07C 61/20
[52] U.S. Cl. .................................. 560/122; 560/126; 560/127; 560/128
[58] Field of Search ........................ 560/122; 562/504

[56] References Cited
U.S. PATENT DOCUMENTS 4,014,919  3/1977  Johnson et al. ...................... 560/122

*Primary Examiner*—James O. Thomas, Jr.
*Assistant Examiner*—L. Hendriksen
*Attorney, Agent, or Firm*—Armstrong, Nikaido, Marmelstein & Kubovcik

[57] ABSTRACT

A 2-cyclopentenone derivative represented by the formula

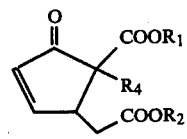

wherein $R_1$ and $R_2$ are lower straight-chain or branched-chain alkyl, alkenyl or aralkyl, and $R_4$ is 2-pentenyl or 2-pentynyl, and process for preparing the same.

3 Claims, No Drawings

2-CYCLOPENTENONE DERIVATIVES

This invention relates to novel 2-cyclopentenone derivatives and a process for preparing the same.

The compounds of this invention are novel compounds represented by the formula

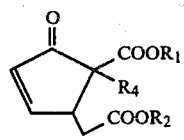
(1)

wherein $R_1$ and $R_2$ are lower straight-chain or branched-chain alkyl, alkenyl or aralkyl, and $R_4$ is 2-pentenyl or 2-pentynyl.

The compounds of this invention are useful as intermediates for the synthesis of jasmonoid compounds which are important as perfumes.

The present compounds can be divided into two groups:

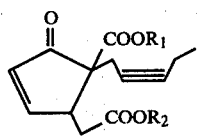 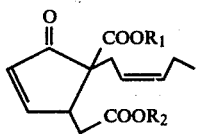

(1-a)   (1-b)

The compounds (1-a) of this invention are prepared easily by subjecting, for example, a 4-acetyl-6-nonynoate derivative of the formula

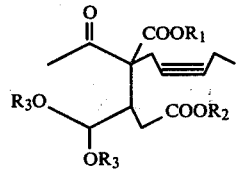
(2)

wherein $R_1$, $R_2$ and $R_3$ are each lower straight-chain or branched-chain alkyl, alkenyl or aralkyl directly to ring closure, or by hydrolyzing the derivative first to obtain a 4-acetyl-3-formyl-6-nonynoate derivative of the formula

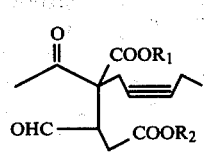
(3)

wherein $R_1$ and $R_2$ are as defined above and subjecting the resulting derivative to ring closure.

The compounds (1-b) of this invention are easily obtained by subjecting a compound (1-a) to cis reduction in the presence of a Lindlar catalyst. The term "cis reduction" as herein used means the reduction by which alkynyl is converted to cis-alkenyl.

The compound (2) which is used as the starting material of this invention is known and prepared for example by the following process.

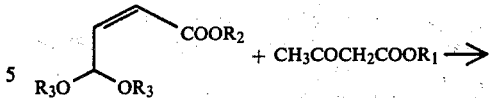

(4)   (5)

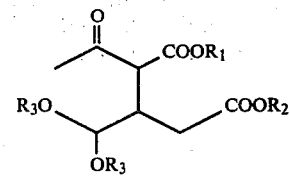

(6)

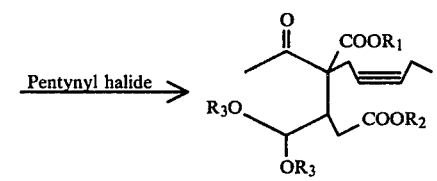

(2)

wherein $R_1$, $R_2$ and $R_3$ are as defined above.

The compound (4) is a cis-2-butenate derivative which is easily prepared for example by electrolytically oxidizing furfuryl alcohol. The compound (2) is obtained by subjecting the derivative and an acetoacetate (5) to condensation to prepare a compound (6) and reacting the compound (6) with pentynyl halide.

The above-mentioned groups $R_1$, $R_2$ and $R_3$ are each lower straight-chain or branched-chain alkyl, alkenyl or aralkyl. Examples of groups $R_1$, $R_2$ and $R_3$ are alkyl groups such as methyl, ethyl, n-propyl, isopropyl, n-butyl, sec-butyl, n-pentyl, neo-pentyl, n-hexyl, iso-hexyl, etc.; alkenyl groups such as vinyl, allyl, 1-propenyl, butenyl, pentenyl, hexenyl, etc; and aralkyl groups such as benzyl, phenetyl, methylbenzyl, phenylpropyl, etc.

The compound (2) is hydrolyzed preferably in the presence of an acid catalyst. Examples of useful acid catalysts are mineral acids such as sulfuric acid, hydrochloric acid and phosphoric acid; peracids such as perchloric acid, perbromic acid and periodic acid; organic sulfonic acids such as benzenesulfonic acid and p-toluenesulfonic acid; acid ion exchange resins; etc. The amount of acid catalyst to be used is not particularly limited but may be suitably determined. Usually about 0.1 to about 10% by weight, preferably about 0.5 to about 2% by weight, of the acid catalyst is used based on the compound (2). Examples of useful reaction solvents are water; tetrahydrofuran, dioxane, ethyl ether and like ethers; methanol, ethanol, propanol and like alcohols; and mixtures of such solvents. The reaction temperature, which is not particularly limited, is usually $-10°$ to $100°$ C., preferably $10°$ to $50°$ C. The reaction time is usually about 6 to about 24 hours although dependent on the reaction conditions.

The compound (2) or (3) is subjected to ring closure reaction preferably in the presence of a salt. Examples of useful salts are organic acid-organic amine salts such as formic acid-morpholine salt, formic acid-piperidine salt, formic acid-pyridine salt, acetic acid-morpholine salt, acetic acid-piperidine salt and acetic acid-pyridine salt. The amount of such a salt to be used, although not particularly limited, is usually about 0.5 to about 2 moles, preferably about 1.1 to about 1.5 moles, per mole of the compound (2) or (3). Examples of preferred reaction solvents are benzene, toluene, xylene and like aromatic hydrocarbons; n-hexane, n-heptane and like aliphatic hydrocarbons; and mixtures of such solvents. The reaction temperature, which is not particularly limited, is usually 50° to 150° C., preferably 70° to 100° C. The reaction time is generally about 3 to about 12 hours although dependent on the reaction conditions. The compounds (1-a) of the present invention are obtained by the process described.

The compounds (1-a) afford compounds (1-b) of the present invention when subjected to cis reduction in the presence of a Lindlar catalyst. Typical of useful Lindlar catalysts is a palladium-calcium carbonate catalyst poisoned with lead acetate and quinoline. The amount of catalyst to be used is not particularly limited but may be suitably determined. Generally 1 to 200% by weight, preferably 10 to 100% by weight, of the catalyst is used based on the compound (1-a). It is preferable to conduct the reaction in an organic solvent. Examples of useful solvents are aliphatic alcohols such as methanol, ethanol and propanol; aliphatic ketones such as acetone, methyl ethyl ketone and methyl isobutyl ketone; aliphatic ethers such as tetrahydrofuran, dioxane and ethyl ether; aliphatic hydrocarbons such as n-hexane and n-heptane; hydrocarbon halides such as dichloroethane; and mixtures of such organic solvents. The reaction may be carried out either at atmospheric pressure or increased pressure. The reaction temperature, which is not particularly limited, is usually 10° to 60° C., preferably 20° to 40° C.

The resulting compounds (1-a) and (1-b) can be easily isolated and purified in the usual manner as by extraction, washing, distillation, chromatography and recrystallization.

The present compounds (1-a) and (1-b) are useful as intermediates for the synthesis of jasmonoid compounds (J) which are important as perfumes. Compounds (J) can be produced from the present compounds by the process illustrated below.

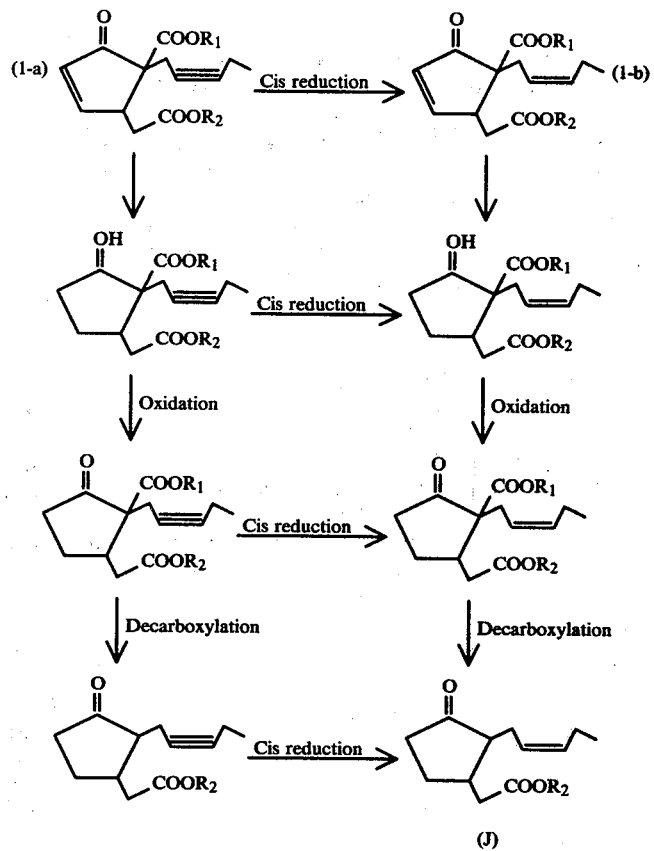

This invention will be described below with reference to Examples and Reference Examples.

REFERENCE EXAMPLE 1

Into a 500-ml reactor are placed 40 g of potassium fluoride, 40 ml of dry tert-butanol, 123 g of methyl cis-4,4-dimethoxy-2-butenate and 36 g of tert-butyl acetoacetate. The mixture is heated at 100° C. with stirring on an oil bath for two days. On completion of the reaction, the tert-butanol is distilled off from the mixture. The residue is dissolved in ethyl acetate, and the solution washed with an aqueous solution of common salt and then dried. The solvent is removed from the product. The resulting residue is purified by a silica gel column and distilled at reduced pressure, giving methyl 4-tert-butoxycarbonyl-3-di-methoxymethyl-5-oxohexanoate (compound (6), $R_1$=t-Bu, $R_2$=$R_3$=$CH_3$) in a yield of 95.4%, b.p. 72°–76° C./0.014 mm Hg.

| Elementary analysis: | C | H |
|---|---|---|
| found (%) | 56.65 | 8/13 |

| Elementary analysis: | C | H |
|---|---|---|
| Calculated (%) | 56.59 | 8.23 |

IR: 2851 cm$^{-1}$ (CH$_3$O), 1736 cm$^{-1}$ (C=O), 1715 cm$^{-1}$ (C=O). NMR (CCl$_4$): 1.43 (bs 9, CH$_3$), 3.19–3.38 (m 6, CH$_3$O), 3.58–3.72 (m 3, CH$_3$OCO), 3.19–3.72 (m 1, CH), 4.31 (t 1, 5Hz, OCHO).

REFERENCE EXAMPLE 2

A 1.38 g quantity of potassium carbonate and 308 mg of potassium iodide are placed into a reactor. Acetone (30 ml) and a solution of 450 mg of methyl 4-tert-butoxycarbonyl-3-dimethoxymethyl-5-oxohexanoate in 10 ml of acetone are further placed into the reactor. Subsequently 270 mg of pentynyl bromide is added to the mixture. The resulting mixture is stirred at room temperature for one hour and thereafter refluxed at 70° C. for 13 hours. On completion of the reaction, the mixture is cooled to room temperature, and the solids are separated off. The product is concentrated in a vacuum, and the residue purified by a silica gel column, giving methyl 4-acetyl-4-tert-butoxycarbonyl-3-dimethoxymethyl-6-nonynoate (compound (2), R$_1$=t-Bu, R$_2$=R$_3$=CH$_3$) in a yield of 91%.

| Elementary analysis: | C | H |
|---|---|---|
| Found (%) | 62.54 | 8.35 |
| Calculated (%) | 61.50 | 8.39 |

IR: 2837 cm$^{-1}$ (CH$_3$O), 1729 cm$^{-1}$ (>C=O), 1710 cm$^{-1}$ (>C=O), 1430 cm$^{-1}$ (CH$_2$), 1354 cm$^{-1}$ (CH$_3$O). NMR (CCl$_4$) (δvalue): 1.11 (3H, CH$_3$-C); 2.26–2.55 (2H, CH$_2$COO); 2.55–2.85 (2H, CH$_2$-C≡); 3.61, 3.65 (6H, CH$_3$OCO); 4.18–4.39

EXAMPLE 1

Methyl 4-acetyl-4-methoxycarbonyl-3-dimethoxymethyl-6-nonynoate (530 mg) is dissolved in 20 ml of tetrahydrofuran, and 25 ml of 1% aqueous solution of perchloric acid is added to the solution. The mixture is stirred at 26° to 28° C. for 12 hours. Subsequently the reaction mixture is neutralized with sodium bicarbonate and concentrated in a vacuum. The residue is extracted with ethyl acetate. The extract is dried and then concentrated to give methyl 4-acetyl-4-methoxycarbonyl-3-formyl-6-nonynoate (compound (3), R$_1$=R$_2$=CH$_3$) in a yield of 98.3%.

NMR (CCl$_4$): 9.65 (CHO).
IR: 2841 cm$^{-1}$ (CHO), 1733, 1716 cm$^{-1}$ (>C=O).

The compound (3) (500 mg) obtained above is dissolved in 200 ml of benzene containing 1 ml of acetic acid and 1 ml of piperidine, and the solution is refluxed for 6 hours. On completion of the reaction, the solvent is removed and the residue dissolved in ethyl acetate. The solution is washed with 10% hydrochloric acid and an aqueous solution of sodium bicarbonate and then dried. The product is concentrated, and the residue purified by a silica gel column, giving 5-methoxycarbonyl-4-methoxycarbonylmethyl-5-(2-pentynyl)-2-cyclopentenone (compound (1-a), R$_1$=R$_2$=CH$_3$) in a yield of 81%, b.p. 110°–115° C./0.15 mm Hg.

| Elementary analysis: | C | H |
|---|---|---|
| Found (%) | 64.64 | 6.30 |
| Calculated (%) | 64.74 | 6.52 |

NMR (CCl$_4$): 1.05 (t, 3, CH$_3$), 1.80–2.30 (m. 2, CH$_2$C≡C), 2.34–2.86 (m. 4, CH$_2$C=C, CH$_2$CO), 3.61, 3.67 (2s, 6, CH$_3$O), 6.14 (dd.1, 6Hz, 2Hz, C=CHCO), 7.59 (dd.1, 6Hz, 2Hz, HC=CCO).

EXAMPLE 2

Methyl 4-acetyl-4-tert-butoxycarbonyl-3-dimethoxymethyl-6-nonynoate (546 mg) is dissolved in 30 ml of tetrahydrofuran, and 25 ml of 1.5% aqueous solution of perchloric acid is added to the solution. The mixture is stirred at 28° C. for 12 hours. Subsequently the reaction mixture is neutralized with sodium bicarbonate and concentrated in a vacuum. The residue is extracted with ethyl acetate. The extract is dried and then concentrated to give methyl 4-acetyl-4-tert-butoxycarbonyl-3-formyl-6-nonynoate (compound (3), R$_1$=t-Bu, R$_2$=CH$_3$) in a yield of 98.0%.

NMR (CCl$_4$): 9.65 (CHO).
IR (neat): 2841 cm$^{-1}$ (CHO), 1733, 1716 cm$^{-1}$ (>C=O), A 790 mg quantity of the compound (3) obtained above is dissolved in 50 ml of benzene containing 1 ml of acetic acid and 1 ml of piperidine, and the solution is refluxed for 4 hours. On completion of the reaction, the solvent is removed, and the residue dissolved in ethyl acetate. The solution is washed with water and an aqueous solution of sodium bicarbonate and thereafter dried. The residue is distilled in a vacuum, giving 5-tert-butoxycarbonyl-4-methoxycarbonylmethyl-5-(2-pentynyl)-2-cyclopentenone (compound (1-a), R$_1$=t-Bu, R$_2$=CH$_3$) in a yield of 78%, b.p. 82°–86° C./0.006 mm Hg.

| Elementary analysis: | C | H |
|---|---|---|
| Found (%) | 67.36 | 7.70 |
| Calculated (%) | 67.48 | 7.55 |

NMR (CCl$_4$): 1.02 (t3, CH$_3$), 1.37 (bs 9, CH$_3$), 1.76–2.73 (m. 6, CH$_2$C≡C, CH$_2$CO), 3.33–3.58 (m.1, CH), 3.66 (s 3, CH$_3$O), 6.10 (dd. 1, 5Hz, 2Hz, C=CHCO), 7.50 (dd. 1, 5Hz, 2Hz, HC=CCO).

EXAMPLE 3

Methyl 4-acetyl-4-methoxycarbonyl-3-dimethoxymethyl-6-nonynoate (530 mg) is dissolved in 50 ml of tetrahydrofuran, and 1 ml of acetic acid and 1 ml of piperidine are added to the solution. The mixture is refluxed for 6 hours. On completion of the reaction, the solvent is removed, and the residue dissolved in ethyl acetate. The solution is washed with 10% hydrochloric acid and an aqueous solution of sodium bicarbonate, then dried and thereafter concentrated. Purification of the residue by a silica gel column affords 5-methoxycarbonyl-4-methoxycarbonylmethyl-5-(2-pentynyl)-2-cyclopentenone (compound (1-a), R$_1$=R$_2$=CH$_3$) in a yield of 70.5%.

EXAMPLE 4

Ethyl 4-acetyl-4-methoxycarbonyl-3-dimethoxymethyl-6-nonynoate (550 mg) is dissolved in 50 ml of benzene, and 1 ml of acetic acid and 1 ml of piperidine are added to the solution. The mixture is refluxed for 10 hours. On completion of the reaction, the solvent is removed, and the residue dissolved in ethyl acetate. The solution is washed with 10% hydrochloric acid and an aqueous solution of sodium bicarbonate, dried and concentrated. The residue is purified by silica gel column, giving 5-methoxycarbonyl-4-ethoxycarbonylmethyl-5-(2-pentynyl)-2-cyclopentenone (compound (1-a), $R_1=CH_3$, $R_2=C_2H_5$) in a yield of 47%.

EXAMPLE 5

A 690 mg quantity of 5-tert-butoxycarbonyl-4-methoxycarbonylmethyl-5-(2-pentynyl)-2-cyclopentenone (compound (1-a)) is dissolved in a mixture of 5 ml of n-hexane and 5 ml of acetone and reduced at room temperature and atmospheric pressure with addition of 3.2 g of a Lindlar catalyst. The catalyst is filtered off from the reaction mixture, and the solvent distilled off. The residue is purified by a silica gel column and distilled in a vacuum, giving 5-tert-butoxycarbonyl-4-methoxycarbonylmethyl-5-(cis-2-pentenyl)-2-cyclopentenone (compound (1-b), $R_1=t$-Bu, $R_2=CH_3$) in a yield of 99.8%, b.p. 81°–84° C./0.005 mm Hg.

| Elementary analysis: | C | H |
| --- | --- | --- |
| Found (%) | 66.91 | 8.36 |
| Calculated (%) | 67.06 | 8.13 |

NMR (CCl$_4$): 0.97 (t. 3, CH$_3$), 1.42 (s. 9, CH$_3$), 2.05 (q, 7Hz, 2, CH$_2$C═C), 2.34–2.71 (m. 4, CH$_2$C═C, CH$_2$CO$_2$), 3.26 (m. 1, 9Hz, CH), 3.66 (s. 3, CH$_3$O), 4.79–5.69 (m. 2, CH═CH), 6.09 (dd. 1, 5Hz, 2Hz, C═CHCO), 7.50 (dd. 1, 5Hz, 2Hz, HC═CCO).

EXAMPLE 6

A 4.5 g quantity of 5-methoxycarbonyl-4-methoxycarbonylmethyl-5-(2-pentynyl)-2-cyclopentenone (compound (1-a)) is dissolved in a mixture of 50 ml of n-hexane and 50 ml of acetone, and 7 g of a Lindlar catalyst is added to the solution. Hydrogen gas is introduced into the solution with stirring. The reaction is completed when the solution has absorbed the theoretical amount of the gas. On completion of the reaction, the catalyst is filtered off from the reaction mixture, and the filtrate is concentrated at reduced pressure. The residue is distilled in a vacuum, affording 5-methoxycarbonyl-4-methoxycarbonylmethyl-5-(cis-2-pentenyl)-2-cyclopentenone (compound (1-b), $R_1=CH_3$, $R_2=CH_3$) in a yield of 99.8%, b.p. 81°–85° C./0.005 mm Hg.

| Elementary analysis: | C | H |
| --- | --- | --- |
| Found (%) | 64.07 | 7.35 |
| Calculated (%) | 64.27 | 7.19 |

NMR (CCl$_4$): 0.97 (t. 3, CH$_3$); 2.05 (q. 2, 7Hz, CH$_2$C═C); 2.27–3.51 (m. 5, CH$_2$C═C, CH$_2$CO, CH); 3.62, 3.66 (2s, 6, CH$_3$O); 4.76–5.75 (m. 2, HC═CH); 6.09 (dd. 1, 5Hz, 2Hz, C═CHCO); 7.47 (dd. 1, 5Hz, 2Hz, HC═CCO).

What is claimed is:

1. A 2-cyclopentenone derivative represented by the formula

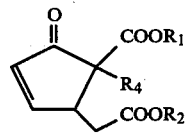

wherein $R_1$ and $R_2$ are lower straight-chain or branched-chain alkyl, alkenyl or aralkyl, and $R_4$ is 2-pentenyl or 2-pentynyl.

2. A 2-cyclopentenone derivative as defined in claim 1 wherein $R_4$ is 2-pentenyl.

3. A 2-cyclopentenone derivative as defined in claim 1 wherein $R_4$ is 2-pentynyl.

* * * * *